US00PP17692P2

(12) United States Plant Patent
Hofmann

(10) Patent No.: US PP17,692 P2
(45) Date of Patent: May 1, 2007

(54) **NEW GUINEA *IMPATIENS* PLANT NAMED 'FISNICS PURSWEET'**

(50) Latin Name: *Impatiens hawkeri*
Varietal Denomination: Fisnics Pursweet

(75) Inventor: Birgit Christa Hofmann, Bendorf (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/330,443

(22) Filed: Jan. 12, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Anne Marie Grunberg
*Assistant Examiner*—Georgia Helmer
(74) *Attorney, Agent, or Firm*—Jondle & Associates P.C.

(57) ABSTRACT

A new New Guinea *Impatiens* plant particularly distinguished by large, round, almost flat bi-colored, purple and pale violet or white flowers on long pedicles, mid season flowering, blackish-green, glossy foliage, and a medium size plant habit that is round and bushy, is disclosed.

1 Drawing Sheet

Genus and species: *Impatiens hawkeri* W. Bull.
Variety denomination: 'Fisnics Pursweet'.

BACKGROUND OF THE NEW PLANT

The present invention comprises a new and distinct cultivar of New Guinea *Impatiens,* botanically known as *Impatiens hawkeri* W. Bull, and hereinafter referred to by the cultivar name 'Fisnics Pursweet'. The new cultivar originated from a hybridization made in the year 2002 in Hillscheid, Germany. The female parent was the proprietary New Guinea *Impatiens* plant 'K00-7244-3' (unpatented), while the male parent was the commercial New Guinea *Impatiens* plant 'Harmony Violet' (patent status unknown). The seeds produced by the hybridization were sown in Moncarapacho, near Faro, Portugal in the late Fall of 2002. A single plant selection was chosen for further evaluation and for asexual propagation in April 2003 in Moncarapacho, Portugal.

The new cultivar was created in 2002 in Hillscheid, Germany and has been asexually reproduced repeatedly by vegetative cuttings and tissue culture in Moncarapacho, Portugal and Hillscheid, Germany over a two year period. 'Fisnics Pursweet' has not been observed under all possible environmental conditions. The present invention has been found to retain its distinctive characteristics through successive asexual propagations.

Plant Breeder's Rights for this cultivar were applied for in Switzerland on Mar. 30, 2005 and in Canada on Apr. 20, 2005.

SUMMARY OF THE INVENTION

The following are the most outstanding and distinguishing characteristics of this new cultivar when grown under normal horticultural practices in Hillscheid, Germany and Langley, British Columbia, Canada.

1. Bi-colored, purple and pale violet or white flower color.
2. Large, round, flat flowers on long pedicels;
3. Uniform, blackish-green, glossy foliage;

4. A medium (to wide) size, round and bushy plant habit; and
5. A mid season flowering response.

DESCRIPTION OF PHOTOGRAPH

This new New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 13- to 14-weeks old, grown in a greenhouse in Hillscheid, Germany, in late Spring.

DESCRIPTION OF THE NEW CULTIVAR

The following detailed descriptions set forth the distinctive characteristics of 'Fisnics Pursweet'. The data which define these characteristics were collected from asexual reproductions carried out in Hillscheid, Germany. The plant history was taken on 11- to 12-week old plants which were planted as rooted cuttings in 12-cm pots in late February 2005, and then grown in a greenhouse at a minimum temperature of 16° C. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens hawkeri* W. Bull.
*Common name.*—New Guinea *Impatiens.*
Parentage:
*Female parent.*—'K00-7244-3,' a proprietary light-violet (weakly bi-colored) flowered New Guinea *Impatiens* plant (unpatented).
*Male parent.*—'Harmony Violet', a violet-purple flowered New Guinea *Impatiens* plant (unpatented).

Growth:

*Growth and branching habit.*—Medium size (becoming mainly wider, not very high), round and bushy; the growth is indeterminate, though weak after the beginning of flowering.

*Height.*—13.0 cm.

*Width.*—24.5 cm.

*Propagation.*—Terminal tips for cuttings.

*Time to produce a finished flowering plant.*—9 to 10 weeks for a 12-cm pot.

*Time to initiate and develop roots.*—18 days at 22° C.

Branches:

*Average number.*—6.3.

*Length of branches.*—10 cm to 14 cm.

*Internode length.*—3.5 cm to 4.0 cm.

*Diameter of branches.*—0.7 cm to 0.8 cm.

*Stem color.*—RHS 185A (dark purple).

Leaves:

*Arrangement.*—Primarily in whorls.

*Size.*—Length: 12.0 cm. Width: 4.9 cm.

*Shape.*—Elliptic.

*Margin.*—Slightly serrate, ciliated.

*Apex.*—Acuminate.

*Base.*—Acute.

*Color (mature leaves).*—Upper surface: RHS N186A (very dark green, almost black). Lower surface: Between RHS 187A to RHS 187B (deep purple).

*Color (immature leaves).*—Upper surface: RHS N186A (very dark green, almost black). Lower surface: Between RHS 187A to RHS 187B (deep purple).

*Texture.*—Surface slightly glossy, often weakly rippled.

*Venation color.*—Upper surface: RHS 51A (pink). Lower surface: RHS 53A (deep red).

*Variegation.*—None.

*Petioles.*—Length: 1.5 cm. Diameter: 0.3 cm to 0.4 cm. Color: Upper surface: RHS 53D. Lower surface: RHS 53A (deep red).

Flower buds:

*Shape.*—Ovoid.

*Size.*—Length: 2.7 cm. Width: 1.6 cm.

*Color.*—From RHS N66A to RHS N74A.

Inflorescence:

*Blooming habit.*—9 weeks after planting of rooted cuttings.

*Inflorescence type.*—Flowers appear solitary in the leaf axils of the upper nodes of the stems.

*Number of flowers per node.*—6 to 9, in various stages of development.

*Flowering season.*—Continuously from March to October, depending on light intensity.

*Lastingness of individual blooms.*—Up to 14 days (in a greenhouse in the Spring at 18° C.).

*Fragrance.*—None.

*Peduncle.*—Color: RHS 154B (light-green); often one side RHS 181B (reddish). Size: Length: 5.5 cm to 6.5 cm. Diameter: 0.1 cm. Texture: Glabrous, flexible.

Flowers:

*Form of corolla.*—Single-type, 5 petals.

*Shape of corolla.*—Nearly round, with the petals overlapping, almost flat.

*Corolla size.*—Length: 7.4 cm. Width: 7.1 cm. Depth: 1.0 cm to 1.2 cm.

Petals:

*Shape.*—Cordate, weakly lobed at the top end.

*Apex.*—Emarginate or retuse.

*Base.*—Attenuate.

*Margin.*—Entire.

*Petal size.*—Top: Length: 3.9 cm. Width: 5.8 cm. Lateral: Length: 4.1 cm. Width: 4.5 cm. Lower: Length: 4.0 cm. Width: 4.8 cm.

*Color.*—General color description: Purple with a pattern of stripes, and between the stripes, a pale violet hue. Upper surface: RHS N74A to RHS N74B, deepest at the banner petal, fading towards the margins of the lateral and lower petals, between the stripes the color is about RHS 74D (somewhat variable). Lower surface: RHS N74A to RHS N74B. Eye Zone: About RHS N66B or RHS N74B (purple), indistinct and small.

*Petal texture.*—Smooth.

*Aspect.*—Flat.

Spur:

*Shape.*—Downwardly curved.

*Color.*—RHS 145D (light-green) near the tip, RHS 62C (light-pink) near the base.

*Size.*—Length: 5.8 cm to 6.5 cm. Diameter: 0.3 cm (at the flower end).

Reproductive organs:

*Stamens.*—Number: 5 fused. Stamen color (upper surface color): RHS N57C (pink). Anthers: Fused, hooded. Pollen color: RHS 8D (whitish-yellow).

*Pistils.*—Style and stigma: 5, very short, RHS 186A (pink). Ovary: 5-celled. Ovary length: 0.5 cm. Ovary color: RHS 186C (surface very dark purple).

Fruit and seed set: No seed set observed.

Disease and insect resistance: No particular resistance or susceptibility has been observed.

COMPARISON WITH PARENTAL AND COMMERCIAL CULTIVARS

'Fisnics Pursweet' differs from the female parent 'K00-7244-3' (unpatented), by having more distinctly bi-colored flowers and somewhat earlier flowering than 'K00-7244-3'.

'Fisnics Pursweet' differs from the male parent 'Harmony Violet' (unpatented), by having variegated flowers of a more purple hue while 'Harmony Violet' has uniform violet flowers and a more compact plant habit.

'Fisnics Pursweet' differs from the commercial cultivar 'Fisnics Burgsweet' (U.S. Plant Pat. No. 16,141) by having a different pattern of flower color. 'Fisnics Pursweet' has finer and more diffuse purple stripes. Additionally, 'Fisnics Pursweet' has larger and wider open flowers and darker foliage color while 'Fisnics Burgsweet' has light lavender ground color with distinct, purple stripes and a large purple splotch on the banner petal.

'Fisnics Pursweet' differs from cultivar 'Kimpgua' (U.S. Plant Pat. No. 10,429) by having larger flowers of a more blurred or diffuse color pattern, and darker, nearly black foliage when compared to 'Kimpgua'.

I claim:

1. A new and distinct cultivar of New Guinea *Impatiens* plant as shown and described herein.

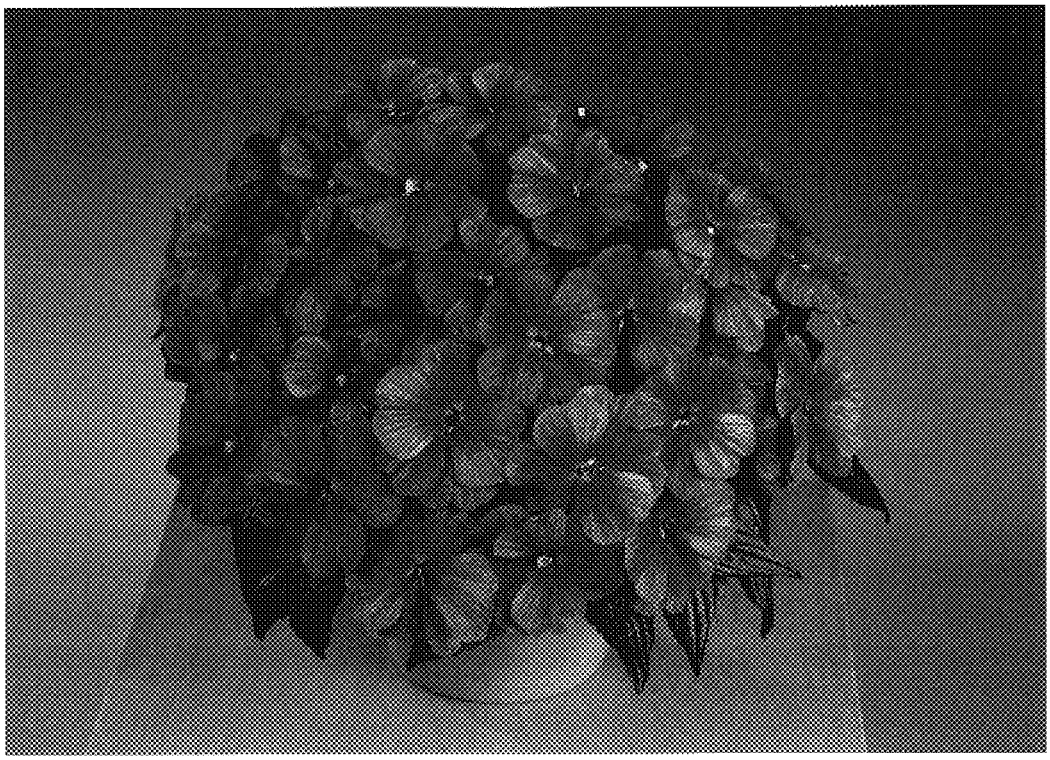

* * * * *